United States Patent

Nies et al.

Patent Number: 5,997,544
Date of Patent: Dec. 7, 1999

[54] PROCESS AND DEVICE FOR PRODUCING STERILE-PACKED BONE CEMENT

[75] Inventors: Berthold Nies, Frankisch Crumbach; Rainer Specht, Babenhausen, both of Germany

[73] Assignee: Merck Patent Gesellschaft mit beschrankter Haftung, Darmstadt, Germany

[21] Appl. No.: 09/069,760

[22] Filed: Apr. 30, 1998

[30] Foreign Application Priority Data

May 2, 1997 [DE] Germany ............... 197 18 648

[51] Int. Cl.⁶ .................................. A61B 17/56
[52] U.S. Cl. ...................... 606/92; 606/93; 606/94
[58] Field of Search ................. 606/92, 93, 94; 523/113, 115, 116, 118

[56] References Cited

U.S. PATENT DOCUMENTS

| 3,079,090 | 2/1963 | Decker | 606/92 |
| 5,558,136 | 9/1996 | Orrico | 606/93 |

FOREIGN PATENT DOCUMENTS

94/16951  8/1994  WIPO .

Primary Examiner—Michael Buiz
Assistant Examiner—Duphna Shai
Attorney, Agent, or Firm—Millen, White, Zelano & Branigan, P.C.

[57] ABSTRACT

A process and device for producing sterile-packed bone cement, wherein the powder component is gas-sterilized in containers that are used for packing.

21 Claims, 1 Drawing Sheet

PROCESS AND DEVICE FOR PRODUCING STERILE-PACKED BONE CEMENT

BACKGROUND OF THE INVENTION

1. Field of the Invention

The present invention relates to a process and a device for producing sterile-packed bone cements. It relates in particular to a process in which a cement powder component is subjected to gas sterilization in the containers that are used for packing.

2. Description of the Related Art

The natural joints in the human body are often subject to degenerative changes resulting, inter alia, in some cases from defects following surgical interventions occasioned by disease or accidents. If these defects have progressed too far, are irreversible or can no longer be treated, it becomes necessary to replace the natural joints or bones by corresponding implants. Examples of bone replacement materials that may be mentioned are shaped implants of a wide variety of kinds, or bone-connecting elements in the form, for instance, of medullary nails, bone screws or osteosynthetic plates. For implantation, these bone replacement materials are anchored in the natural bone using bone cements.

Customary bone cements are composed of a solid component, which consists of a finely divided polymer of acrylic and/or methacrylic esters and of further additives, such as polymerization catalysts, together, if desired, with X-ray contrast media, fillers and colorants, and of a liquid component, which consists of an acrylic and/or methacrylic ester monomer and of further additives such as polymerization accelerators and stabilizers. The polymer powder component of the cement consists preferably of granular particles with a spherical shape. The particle size preferably lies within a narrow range or is substantially uniform.

For use, the solid component and the liquid component are combined to form a liquid to semisolid paste. This paste is optionally brought in to a desired shape or is applied at the implantation site of a prosthesis in order to cement it in. The composition cures by means of the polymerization reaction induced with the mixing of the components. The bone cement is judiciously provided in a form which brings together separate containers, with matched amounts of the two components, in a single pack unit.

There are various possibilities for the separate packing of the individual components for preparing bone cement. For example, the sterile polymer powder can be packed into polyethylene pouches, while the liquid component is subjected to sterile filtration and dispensed, for example, into glass ampoules.

There are also packs which consist of flexible films and which possess two or more separate chambers separated from one another by removable seals. To mix the ready-to-use bone cement, the seal is removed or opened and the components are mixed homogeneously by kneading the flexible pouches. A system of this kind is described, for example, in the document WO 94/16951.

Also known are packs which are constructed as just described but which additionally possess a vacuum reservoir, attached to the powder container, and where the powder is packed under vacuum. The vacuum pack has the advantage that when the cement is mixed less air is incorporated into the bone cement, which has a positive effect on the porosity of the cement. Furthermore, the presence of a vacuum reservoir makes the full mixing of the polymer powder with the monomer, after the sealing device has been opened, much simpler and more effective, since the reduced pressure in the powder container draws the monomer right in under suction.

The individual components for preparing the bone cement must of course be packaged in a sterile manner. The customary sterilization techniques include chemical sterilization techniques, such as gassing with ethylene oxide, and sterilization by means of high-energy radiation, usually γ radiation or β radiation.

In the case of the closed cementing systems, and especially in the case of vacuum-packed cement powders, the individual components have, to date, either been sterilized by one of the above sterilization techniques, prior to dispensing, and then dispensed into the respective containers by way of sterile filters—in other words, aseptic dispensing is practiced—or the components have been sterilized within the packs by irradiation.

It is known, however, that high-energy radiation has a great effect on the properties of the bone cement. In particular, the viscosity is altered for the worse, and the shelf life has also been found, by our own investigations, to suffer a decrease.

It is known, however, that high-energy radiation has a great effect on the properties of the bone cement. In particular, the viscosity is altered for the worse, and the shelf life has also been found, by our own investigations, to suffer a decrease.

SUMMARY OF THE INVENTION

An object of the present invention, therefore, is to prepare sterile-packed bone cement in which the sterility of the powder component is not realized by high-energy radiation or aseptic dispensing, where there may be deficient sterility.

Upon further study of the specification and appended claims, further objects and advantages of this invention will become apparent to those skilled in the art.

A process and a device have now been found in which a bone cement powder and the corresponding containers are subjected internally to gas sterilization, and, if desired, the container holding the polymer component is subsequently evacuated without losing the sterility.

The invention hence provides a process for producing sterile-packed bone cement, which process is characterized in that the polymer powder is introduced into a separate container, which is used for packing and which is connected via a sealing device to a further container for the monomer, and the said powder is subjected, by way of corresponding sterile filters, to gas sterilization, the second container for the monomer likewise being sterilized internally.

The invention also provides a process for producing sterile-packed bone cement, comprising providing a first and second containers connected but having an opening therebetween sealed by a first sealing device, wherein the first container contains a polymer powder and the second container contains a monomer; introducing sterilizing gas via a first sterile filter attached to the first container so as to sterilize the polymer powder in the first container; and, introducing the sterilizing gas via a second sterile filter attached to the second container so as to sterilize the second container internally.

The invention also provides a device for producing sterile-packed bone cement, in which the sterility is achieved by gas sterilization, characterized in that this device comprises:

a polymer powder container which is used for packing and which is connected on one side, via a sealing device, to a second container for the monomer and, on the other side, connected via a separation area, to a sterile filter the polymer powder being subjected to gas sterilization in this container, it being possible to dispose, if desired, between the polymer container and the separation area an expansion of vacuum reservoir of sufficient size which communicates with the polymer container via a powder filter;

a second container for the monomer, which is connected on one side via a sealing device to the polymer container and, on the other side, connected via a separation area to a sterile filter, and which is likewise sterilized internally in the course of the gas sterilization;

optionally, an additive container for a further, liquid or solid component that is added to the monomer before it is mixed with the polymer powder, this container being arranged between the monomer container and the sterile filter by way of a sealing device and being likewise sterilized internally in the course of the gas sterilization.

The invention also provides a device for producing sterile-packed bone cement, useful for achieving sterility by gas sterilization, which comprises:

a first container for packing polymer powder;

a second container for packing monomer, the first container being connected to the second container via a first sealing device;

a first sterile filter connected to the first container via a first separation area;

a second sterile filter connected to the second container via a second separation area;

the device optionally comprises a reservoir of result-effective size, located between the first separation area and a powder filter in communication with the first container, for creating suction via pressure difference between the first container and the second container when the first sealing device is open to draw the monomer from the second container into the first container for mixing with the polymer powder; the reservoir is preferably a vacuum or expansion reservoir.

The device further optionally comprises an third additive container for holding a solid or liquid component that is to be added to the monomer before mixing the monomer with the polymer powder, the third container is connected to the second container via a second sealing device.

The device allows the polymer powder, the first container, the second container, the monomer and optional the reservoir and third container to be sterilized internally during the course of gas sterilization.

The above-described containers used as packing or as a vacuum pack are flexible and are preferably constructed of a film material comprising a monomer-resistant polymer. For the present invention it is possible to employ single or multilayer materials, composites of various polymers, and also composites comprising polymers with non-organic plies (e.g., aluminum foil).

The material ultimately used depends on the substances that are to be packaged and the conditions under which the materials are initially mixed. For many substances a polyethylene film is suitable. Examples of other suitable materials are Teflon, polyesters, nylon, ethylene-vinyl alcohol, metal foil or various combinations of these materials. Usually, thermoplastic films are employed and the containers are produced by welding the film edges.

DETAILED DESCRIPTION

Figure 1:
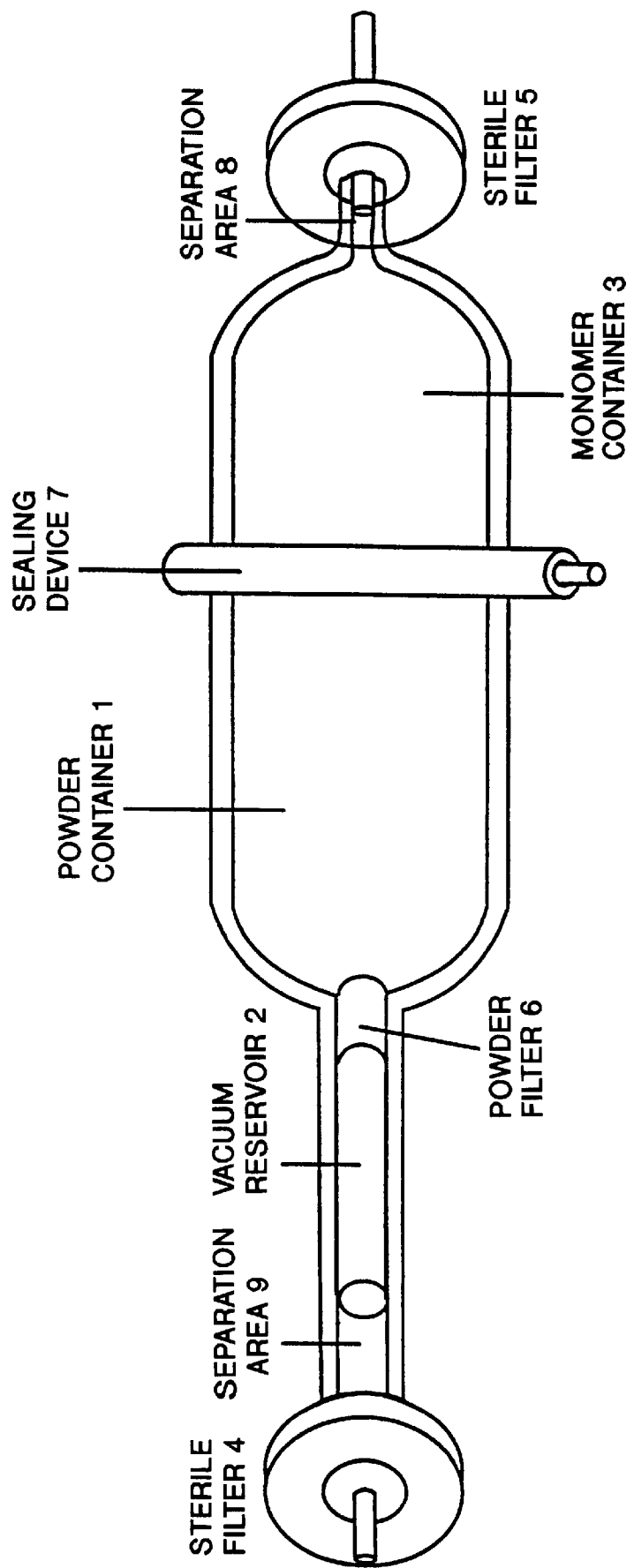
FIG. 1 is a diagram showing the components of a preferred embodiment of the sterile-packed bone cement device.

FIG. 1 is intended to illustrate, in a simple, diagrammatic fashion, a particularly preferred embodiment of the device suitable for the process of the invention. On the left-hand side, a powder container (1) is connected by way of a powder filter (6) to an expansion or vacuum reservoir (2), which in turn is connected to a sterile filter (4). Between the vacuum reservoir (2) and the sterile filter (4), there is a separation area (9) which serves to provide a gas tight closure of the powder container after the sterilization techniques described herein have been implemented. Alternatively, the powder container (1) can be connected directly via the separation area (9) to the sterile filter (4) without the intermediate vacuum reservoir (4).

On the right-hand side, the powder container (1) is connected via a sealing device (7) with a monomer container (3), which has a separation area (8) and a sterile filter (5).

It is possible, if desired, for there to be a further container, by way of a sealing device, between the monomer container (3) and the separation area (8). This container may hold a third component for producing the bone cement or for admixing the bone cement.

The sealing devices between the containers must be able to be closed easily and opened again or completely removed. Various such devices are known. It is preferred to use clamps of a wide variety of kinds for dividing two containers and which can be removed again easily when required. A heat seal or adhesive seal can also be used. The strength of these closures must be chosen such that the seals can be broken by applying pressure to one of the containers without, of course, the sealed seams of the containers themselves bursting open.

An example of a particularly preferred sealing device is an approximately semicircular clamp with a cylindrical rod. The tubular film is clamped therebetween and produces a tight seal between the respective containers. For opening, the cylindrical rod is removed. Similar clamp systems are described, for example, in WO 94/16951.

The expansion or vacuum reservoir (2) is connected via a powder filter (6) to the polymer container, which in an alternative embodiment the expansion or vacuum reservoir can also be disposed within the polymer container.

This reservoir is referred to as an expansion reservoir if packing is carried out under atmospheric pressure and as a vacuum reservoir when vacuum packing is carried out, i.e., when the polymer container, following the implementation of gas sterilization and degassing, is additionally evacuated, which is particular preferred.

This expansion or vacuum reservoir must in each case be of an adequate or result-effective size in order to be able to accommodate the gases which may be evolved when the seal between powder and monomer container is opened and the two components are mixed. For better initial mixing, preference is given to the presence of such an expansion or vacuum reservoir.

Particular preference is given to packing under vacuum with the presence of a vacuum reservoir. The pressure difference between the evacuated powder container and the monomer container results in very good mixing of the two components. Without the vacuum reservoir, the reduced pressure present between the powder particles would in many cases not be sufficient to draw all of the monomer, under suction, into the powder. The function of the vacuum reservoir is therefore to maintain a sufficiently low pressure in the powder container until initial mixing is complete.

Following initial mixing, the vacuum reservoir or, in the alternative case, the expansion reservoir is removed and the cement can be discharged for use. It is judicious to supplement a sterile-packed cement of this kind by a device for applying the bone cement. Corresponding devices are known and customary. Consequently, the pack holding the initially mixed cement can also be inserted into a bone cement syringe or gun and the cement discharged in this way. This method is known from the literature and is described, for example, in WO 94/16951, although it is also well known to the skilled worker from numerous other sources.

The sterile and powder filters used herein are standard components which are in accordance with the prior art and are known to every skilled worker in this field. No further elucidation is therefore necessary.

In one preferred embodiment the sterilization technique of the invention is conducted as follows. First, the sterile filter (5) is mounted and then the sealing device (7) is sealed. The powder container (1) is then filled from the right-hand side, before inserting, in succession, the powder filter (6) and the sterile filter (4). The polymer powder component is then introduced through the monomer container (3) into the powder container (1). This prevents residues of powder remaining in the monomer container in the course of filling, which might then react prematurely with the monomer. The powder-filled container is finally subjected to sterilization. To this end the material to be sterilized is placed in a chamber and the sterilizing gas, preferably gaseous ethylene oxide, is admitted to the chamber. This gas acts on the material to be sterilized for a number of hours; the period of sterilization can be between one hour and 24 hours. By way of the sterile filter, the gas is here able to penetrate into all of the container cavities. This means that the monomer container (3) is also sterilized internally.

Another, particularly preferred variant is to proceed as just described and to place the material to be sterilized in a chamber. Then, however, the chamber is evacuated before the sterilization gas is admitted to the chamber. The subsequent procedure is then as described above.

Thereafter, the ethylene oxide gas is preferably pumped off or discharged. For this purpose the sterilized material is placed in a degassing chamber where it is degassed for a period of 1–50 days, partly under standard conditions and partly with vacuum. As soon as a residual gas concentration of about 1 ppm has been reached, the powder container is also given a gas tight seal on the right-hand side at the separation (9), by means, for example, of sealing, i.e., by thermal melting of the film pouch (using a film welding device, for example).

With a view to the quality of the cement and to the operation of initial mixing, however, the air which is still present is pressed out before sealing at the separation area (9), or the powder container is evacuated via the right-hand sterile filter. On reaching the desired vacuum, which is preferably 0.01–0.2 bar, the container is then sealed at the separation area (9) as just described. This variant embodiment of the evacuation, which leads to vacuum packing of the polymer component, is very particularly preferred.

Subsequently, the sterile monomer is dispensed through the sterile filter (5), by way for example of a penetrating cannula, into the internally sterilized monomer container. Then, preferably, the remaining air is removed, which can take place by pressing it out or drawing it off under suction, and then this container too is closed at the separation area (8) by sealing, for example.

When this is done, the cement components are sterilized and packed or vacuum-packed. Subsequently, in a preferred embodiment of the invention, the container in the secondary pack is also sterilized externally by means of ethylene oxide gassing.

Another embodiment of the present invention features a third container (additive container) which is located preferably between sterile filter (5) or separation area (8) and the monomer container (3), the two containers being connected to one another by a removable closure mechanism comparable with the sealing device (7). This additive container can then be employed if it is intended to add a further component for initial mixing of the cement. This third component can be liquid or solid in nature and is added to the monomer before the latter is mixed with a powder.

The sterilization technique is practiced as already described, except that, after the dispensing of the monomer and, if appropriate, after removal of the air from this container, the seal between monomer container and additive container is closed, then the sterilized third component is introduced via the sterile filter, and sealing is carried out at the separation area (8) after removal of the air.

For mixing, the connection between the additive container and the monomer container is first of all opened. After homogeneous mixing, the connection between powder and monomer is then opened and the cement is mixed homogeneously.

Depending on the cement formulation, it may also be useful or necessary in the course of mixing to enhance the mixing effect by kneading the flexible container.

The amounts of individual components are judiciously matched precisely to one another. In the case of the customary cements the ratio between powder and monomer preferably lies in a range of from 1.5:1 to 2.5:1.

The bone cement powder normally comprises the known polymers and also polymerization initiators (which may be present within the polymer), and may also include X-ray contrast media, fillers, colorants and, if desired, antibiotics or further active ingredients as well. The monomer component may also comprise polymerization accelerators or stabilizers.

When preparing certain bone cements it may be desirable or even necessary to dispense third components, such as active ingredients or the other additives already mentioned, separately into the above-described additive container. In this case, as already mentioned, this third component is then mixed initially with the monomer prior to mixing of the later with the polymer powder. This third component, too, is judiciously packed in the appropriate amount. For example, a third component can be added in an amount which lies within the range between 5% and 20% of the monomer weight.

A possible example which can be used here is the preparation of an MTX cement. MTX cement is a cement which, in addition to the customary cement components, contains a further component, the cytostatic agent methotrexate. This component can be added as a solution in, for example, vinylpyrrolidone. Following the implanting of the cement, this cytostatic agent is released at the cement matrix and can be used for local treatment of bone tumors, for examples.

The present invention therefore provides an outstanding process for the sterile packing or sterile vacuum packing of cement components, with the powder component being sterilized by gas sterilization in the container used for packing. The adverse effects which occur through sterilization with high-energy radiation are overcome in this case. As a result, the mixed cements are of substantially improved quality.

Without further elaboration, it is believed that one skilled in the art can, using the preceding description, utilize the present invention to its fullest extent. The preceding specific embodiments are, therefore, to be construed as merely illustrative, and not limitative of the remainder of the disclosure in any way whatsoever.

The full disclosure content of all applications, patents, and publications cited above and below, and of corresponding German application 197 18 648.3, are hereby incorporated into this application by reference.

EXAMPLE 1

The device used is like that of FIG. 1.

40 g of the powder, consisting of polymethyl acrylate (PMA) /polymethyl methacrylate (PMMA) copolymer, $ZrO_2$, and benzoyl peroxide (BPO), are introduced into the apparatus described above by way of preference. This apparatus is placed in a chamber, the chamber is evacuated, and ethylene oxide gas is admitted to the chamber. The gas is allowed to act on the material to be sterilized for about 20 hours.

Subsequently, the ethylene oxide gas is pumped off. The sterilized device is placed in a degassing chamber where it is degassed under standard conditions until the residual gas concentration is about 1 ppm. The powder container is subsequently evacuated via the sterile filter (4). On reaching the desired vacuum, the powder container is sealed at the separation area (9).

Then 20 ml of the sterile monomer component MMA+ dimethyl-para-toluidine (DMPT) are inserted through the sterile filter (5) into the likewise internally sterilized monomer container. After forcing out the remaining air, this container too is closed by sealing at the intended separation area (8).

The cement components have thus been vacuum-packed in a sterile fashion. The container can subsequently be sterilized externally as well in the secondary packing, by gassing with ethylene oxide.

EXAMPLE 2

An apparatus like that of FIG. 1 is used, supplemented by an additive container which is disposed on the left-hand side of the monomer container via a sealing device like that of (7).

As described in Example 1, 40 g of the powder component, comprising PMA/PMMA copolymer, $ZrO_2$ and BPO, are initially dispensed and then the procedure of Example 1 is followed up to the point of evacuating and sealing the powder container. Then, 20 ml of the monomer component, comprising MMA+DMPT, are dispensed as in Example 1, and, after the remaining air has been forced out, the sealing device between the monomer container and the additive container is closed. Subsequently, the sterilized third component, 2 ml of methotrexate solution, is introduced via the sterile filter (5), and then the separation area (8) is sealed off.

If desired, the container in the secondary packing can be sterilized externally by gassing with ethylene oxide.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for producing sterile-packed bone cement, comprising:

providing a first and second containers connected but having an opening therebetween sealed by a first sealing device, wherein said first container contains a polymer powder and said second container contains a monomer;

introducing sterilizing gas via a first sterile filter attached to said first container so as to sterilize said polymer powder in said first container; and, introducing the sterilizing gas via a second sterile filter attached to said second container so as to sterilize said second container internally.

2. The process according to claim 1, further comprising:

degassing said first and second containers by way of said first and second sterile filter; and, sealing said first container at a first separation area between said first container and said first sterile filter.

3. The process according to claim 2, further comprising:

introducing sterile monomer into said sterilized second container by way of said second sterile filter; and, sealing said second container at a second separation area between said second sterile filter and said second container.

4. The process according to claim 2, wherein the degassing is performed in a degassing chamber.

5. The process according to claim 1, further comprising:

evacuating said sterilizing gas from said first container by way of said first sterile filter; and, sealing said first container at a first separation area between said first container and said first sterile filter.

6. The process according to claim 1, further comprising:

optionally utilizing a third container for containing a solid or liquid additive component, said third container is located between said second sterile filter and said second container and is connect to said second container via a second sealing device.

7. The process according to claim 6, further comprising:

utilizing a reservoir of result-effective size attached to said first container to create suction via pressure difference between said first container and said second container when said first sealing device is open to draw said monomer from said second container into said first container for mixing with said polymer powder.

8. The process according to claim 7, further comprising:

sterilizing the sterile-packed cement packaging components externally in a secondary packaging.

9. The process according to claim 7, wherein said reservoir is an expansion reservoir.

10. The process according to claim 7, wherein said reservoir is a vacuum reservoir.

11. The process according to claim 7, wherein result-effective size reservoir is a reservoir that effectively accommodates gases that evolve when said polymer powder and said monomer are mixed and create suction to draw said monomer from said second container into said first container when said first sealing device is open.

12. The process according to claim 1, wherein said sterilizing gas is ethylene oxide gas.

13. The process according to claim 1 wherein said sealing device is re-closeable, re-openable, and removable.

14. A device for containing sterile-packed bone cement, wherein sterility is achieved by gas sterilization, said device comprising:

a first container for packing polymer powder;

a second container for packing monomer, said first container being connected to said second container via a first sealing device;

a first sterile filter connected to said first container via a first separation area;

a second sterile filter connected to said second container via a second separation area;

a reservoir, located between said first separation area and a powder filter in communication with said first container, for creating suction via pressure difference between said first container and said second container when said first sealing device is open to draw said monomer from said second container into said first container for mixing with said polymer powder; and whereby The device is effective for sterilizing the polymer powder, said first container, said second container, the monomer, and the reservoir internally by gas sterilization.

15. The device according to claim 14, wherein said first and second containers are made of polymer films and are suitable for vacuum packing.

16. The device according to claim 14, wherein said reservoir is an expansion reservoir.

17. The device according to claim 14, wherein said reservoir is a vacuum reservoir.

18. The device according to claim 14, wherein said first sealing device is recloseable, re-openable, and removable.

19. The device according to claim 14, wherein said reservoir is of a size effective to accommodate gases that evolve when said polymer powder and said monomer are mixed and create suction to draw said monomer from said second container into said first container when said first sealing device is open.

20. A device for containing sterile-packed bone cement according to claim 14, further comprising:

a third additive container for holding a solid or liquid component that is to be added to the monomer before mixing the monomer with the polymer powder, said third container is connected to said second container via a second sealing device; and, whereby the device is also effective for sterilizing the third container internally by gas sterilization.

21. A device for containing sterile-packed bone cement according to claim 20, wherein said third container is made of polymer film and is suitable for vacuum packing.

* * * * *